US006770472B2

(12) United States Patent
Manalis et al.

(10) Patent No.: US 6,770,472 B2
(45) Date of Patent: Aug. 3, 2004

(54) DIRECT DNA SEQUENCING WITH A TRANSCRIPTION PROTEIN AND A NANOMETER SCALE ELECTROMETER

(75) Inventors: Scott R. Manalis, Santa Barbara, CA (US); Stephen C. Minne, Danville, IL (US); Calvin F. Quate, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 168 days.

(21) Appl. No.: 09/993,338

(22) Filed: Nov. 13, 2001

(65) Prior Publication Data

US 2002/0086318 A1 Jul. 4, 2002

Related U.S. Application Data

(60) Provisional application No. 60/253,315, filed on Nov. 17, 2000.

(51) Int. Cl.$^7$ .......................... C12M 1/34; G01N 27/26
(52) U.S. Cl. ................................. 435/287.2; 435/288.3; 204/403.03; 204/403.13
(58) Field of Search ....................... 204/403.01, 403.03, 204/403.13; 435/6, 7.1, 23, 287.2, 288.3; 257/14, 24, 30

(56) References Cited

U.S. PATENT DOCUMENTS

| 5,731,598 A | * | 3/1998 | Kado et al. .................... 257/30 |
| 5,827,482 A | * | 10/1998 | Shieh et al. ............. 422/82.02 |
| 5,959,095 A | * | 9/1999 | Martinelli et al. ....... 536/24.32 |
| 6,238,871 B1 | | 5/2001 | Koster ............................ 435/6 |
| 6,280,939 B1 | | 8/2001 | Allen ............................. 435/6 |

OTHER PUBLICATIONS

Schafer et al. (1991); "Transcription of single moecules of RNA polymerase observed by light microscopy;" Nature 352, p. 444.

Yin et al. (1995); "Tanscription against an applied force;" Science 270, p. 1653.

K. K. Likharev; "Single–electron devices and their applications;" PROC. of the IEEE vol. 87 No. 4, Apr. 1999, p. 606.

Yoo et al. (1997); "Scanning single electron transistor microscopy imaging individual charges;" Science 276, p. 579.

Schoelkopf et al. (1998); "The radio–frequency single electron transistor: a fast and ultrasensitive electrometer;" Science 280, p. 1238.

Kazuhiko Matsumoto et al.; "Application of scanning tunneling microscopy nanofabrication process to single electron transistor;" J. Vac. Sci. Technol. B14(2), Mar./Apr. 1996, p. 1331.

Michel H. Devoret et al.; "Single–electron transfer in metallic nanostructures;" Nature, vol 360, Dec. 10, 1992.

* cited by examiner

*Primary Examiner*—David A. Redding
(74) *Attorney, Agent, or Firm*—Lumen Intellectual Property Services, Inc.

(57) ABSTRACT

The present invention provides an apparatus and method for nucleotide or DNA sequencing by monitoring the molecular charge configuration as the DNA moves through a protein that is capable of transcribing the DNA. The apparatus and method provides a nanoscale electrometer that immobilizes the protein. The protein receives the DNA and transcribes the DNA. The nanoscale electrometer is a sensitive device that is capable of sensing and measuring the electronic charge that is released during the transcription process. The apparatus and method of the present invention further provides monitoring means that are attached to the nanoscale electrometer to monitor the electronic charge configuration as the DNA moves through the protein. Once the electronic charge configuration is established, a correlation is computed, using computing means, between the electronic charge configuration and a nucleotide signature of the DNA.

18 Claims, 4 Drawing Sheets

400

500

DIRECT DNA SEQUENCING WITH A TRANSCRIPTION PROTEIN AND A NANOMETER SCALE ELECTROMETER

CROSS-REFERENCE TO RELATED APPLICATIONS

This application is cross-referenced to and claims priority from U.S. Provisional application No. 60/253,315 filed Nov. 17, 2000, which is hereby incorporated by reference.

U.S. GOVERNMENT RIGHTS

This invention was made with U.S. Government support under contract. No. ECS-9522195 awarded by the National Science Foundation. The U.S. Government has certain rights in this invention.

FIELD OF THE INVENTION

This invention relates generally to an apparatus and method for DNA sequencing. More particularly, it relates to an apparatus and method for DNA sequencing based on the direct observation of polymerase with a nanometer scale electrometer.

BACKGROUND

DNA sequencing is a major challenge. For instance, the process of determining the exact order of the 3 billion chemical building blocks making up the DNA of the 24 different human chromosomes has been and still is the greatest technical challenge in science and technology. The resulting DNA sequence maps will help reveal the estimated 100,000 human genes within our DNA as well as the regions controlling them that can then be used by $21^{st}$ century scientists to explore human biology and other complex phenomena.

Transcription is the process by which the nucleotide sequence of DNA is replicated into RNA. Transcription starts with unwinding DNA at the beginning of a gene. Then nascent RNA is synthesized by a complementary base pairing with the template strand of DNA. The synthesis site moves along template DNA. Further reference for the transcription process can be found in a book by Paul Berg and Maxine Singer, entitled "*Dealing with Genes*", published by University Science Books, Mill Valley, 1990. This process is accomplished with a class of proteins called RNA polymerases. These proteins directly replicate the sequence of a template strand of DNA by constructing a nascent RNA strand from individual nucleotides. Transcription occurs when the RNA polymerase binds to a discrete DNA sequence that defines the beginning of a given gene. The discrete sequence, known as a promoter region, signals the RNA polymerase to separate the two strands of the DNA and begin replicating one of the strands into a strand of nascent DNA. Each nucleotide that is added to the nascent RNA is determined by complementary base pairing with successive nucleotides of the template DNA. For example, an A, G, T, or C in the DNA template strand correspond to a U, C, A or G in the nascent RNA strand. The polymerase moves along the template DNA while it continues to add nucleotides to the nascent RNA until the end of the gene is reached. At this point, the transcription is terminated and the completed strand of RNA is released.

The movement of RNA polymerase relative to the template DNA has been previously observed both by force detection and optical methods. Schafer et al. (1991) in a paper entitled "*Transcription of single molecules of RNA polymerase observed by light microscopy*", published in Nature 352, page 444, observed transcription by a single RNA polymerase molecule using light microscopy to detect the Brownian motion of a gold particle that was attached to the template. Analysis of the Brownian motion enabled Schafer et al. to measure the movement of the template DNA relative to the polymerase molecule. Yin et al. (1995) in a paper entitled "Transcription against an applied force", published in Science 270, page 1653, demonstrated that the force produced by a single RNA polymerase could be measured with an optical trap. At the start of the transcription, the RNA polymerase is immobilized on a glass slide. One end of the template DNA is attached to a polystyrene bead in the optical trap while the other end is bound to the polymerase. During transcription, force exerted by the polymerase on the bead was monitored as a function of time by measuring the bead position with an interferometer. While both of these experiments give direct evidence that the RNA is indeed replicating, they do not detect specific nucleotide sequence.

U.S. Pat. No. 6,280,939 to Veeco Instruments, Inc. teaches a method and apparatus for DNA sequencing using a local sensitive force detector that is performed in real time using an atomic force microscope (AFM). The AFM's probe detects motions that occur when a polymerase incorporates nucleotides into a growing polynucleotide chain and a newly formed double-stranded polynucleotide helix translocates (or "ratchets") through the polymerase's reaction site. These motions generate a mechanical force that is reflected, either directly or indirectly, by motion of the AFM cantilever. The resulting changes in cantilever motion are detected and can be recorded as an indication that a nucleotide has been incorporated into the DNA template. To determine which nucleotide type has been incorporated, a characteristic of the incorporation of at least one nucleotide type of interest is flagged so as to be distinguishable from the corresponding characteristics of the incorporation of nucleotides of other types.

U.S. Pat. No. 6,238,871 to Sequenom, Inc. teaches a method to sequence DNA by mass spectrometry. The improvements of this method over the existing DNA sequencing technologies are high speed, high throughput, no electrophoresis and gel reading artifacts due to the complete absence of an electrophoretic step, and no costly reagents involving various substitutions with stable isotopes. U.S. Pat. No. 6,238,871 utilizes the Sanger sequencing strategy and assembles the sequence information by analysis of the nested fragments obtained by base-specific chain termination via their different molecular masses using mass spectrometry, as for example, MALDI or ES mass spectrometry. A further improvement U.S. Pat. No. 6,238,871 teaches is the throughput that can be obtained by introducing mass-modifications in the oligonucleotide primer, chain-terminating nucleoside triphosphates and/or in the chain-elongating nucleoside triphosphates, as well as using integrated tag sequences which allow multiplexing by hybridization of tag specific probes with mass differentiated molecular weights.

Accordingly, the demand and importance of DNA sequencing continuously requires the emergence of new methods and techniques that allow for increased DNA sequencing speed and reliability.

SUMMARY OF THE INVENTION

The present invention provides an apparatus and method for nucleotide or DNA sequencing by monitoring the molecular charge configuration as the DNA moves through a protein, for instance a RNA polymerase, that is capable of transcribing the DNA. The apparatus and method provides a nanoscale electrometer that immobilizes the protein. The protein receives the DNA and transcribes the DNA. The nanoscale electrometer is a sensitive device that is capable of sensing and measuring the electronic charge that is released during the transcription process. The apparatus and method of the present invention further provides monitoring means that are attached to the nanoscale electrometer to monitor the electronic charge configuration as the DNA moves through the protein. Once the electronic charge configuration is established, a correlation is computed, using computing means, between the electronic charge configuration and a nucleotide signature of the DNA. The present invention provides two exemplary embodiments for nanoscale electrometers; first a single electron transistor and second a nanoparticle device. In case of the single electron transistor, the protein is immobilized on the gate of the single electron transistor to receive the DNA. In case of the nanoparticle device, which includes two electrodes and a nanoparticle positioned in between the two electrodes, the protein is immobilized on the nanoparticle to receive the DNA.

The method of the present invention for sequencing DNA provides the steps of immobilizing a protein that is capable of transcribing DNA on a nanoscale electrometer and delivering the DNA to the protein. The method further provides the step of monitoring an electronic charge configuration at the nanoscale electrometer as the DNA moves through the protein. The method also includes the step of computing, using computing means, a correlation between the electronic charge and a nucleotide signature of the DNA.

The present invention further provides an integrated circuit chip for sequencing one or more DNA samples. The integrated circuit chip includes a plurality of interconnected nanoscale electrometers and a plurality of proteins that are capable of transcribing one or more DNA samples. The proteins are immobilized on the interconnected nanoscale electrometers to receive and transcribe one or more DNA samples.

The present invention further provides a method for sequencing one or more DNA samples with the steps of immobilizing a plurality of proteins that are capable of transcribing DNA samples on a plurality of nanoscale electrometers and delivering the DNA samples to the proteins. The method further provides the step of monitoring electronic charge configurations at the nanoscale electrometers as the DNA moves through the proteins. The method also provides the step of computing one or more correlations between the electronic charge configurations and nucleotide signatures of the DNA.

In view of that which is stated above, it is an objective of the present invention to provide an apparatus and method for DNA sequencing with a transcription protein and a nanoscale electrometer. An advantage of the present invention over the prior art is that the system enables one to directly measure the DNA sequence as the transcription process unfolds.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Figure 1:
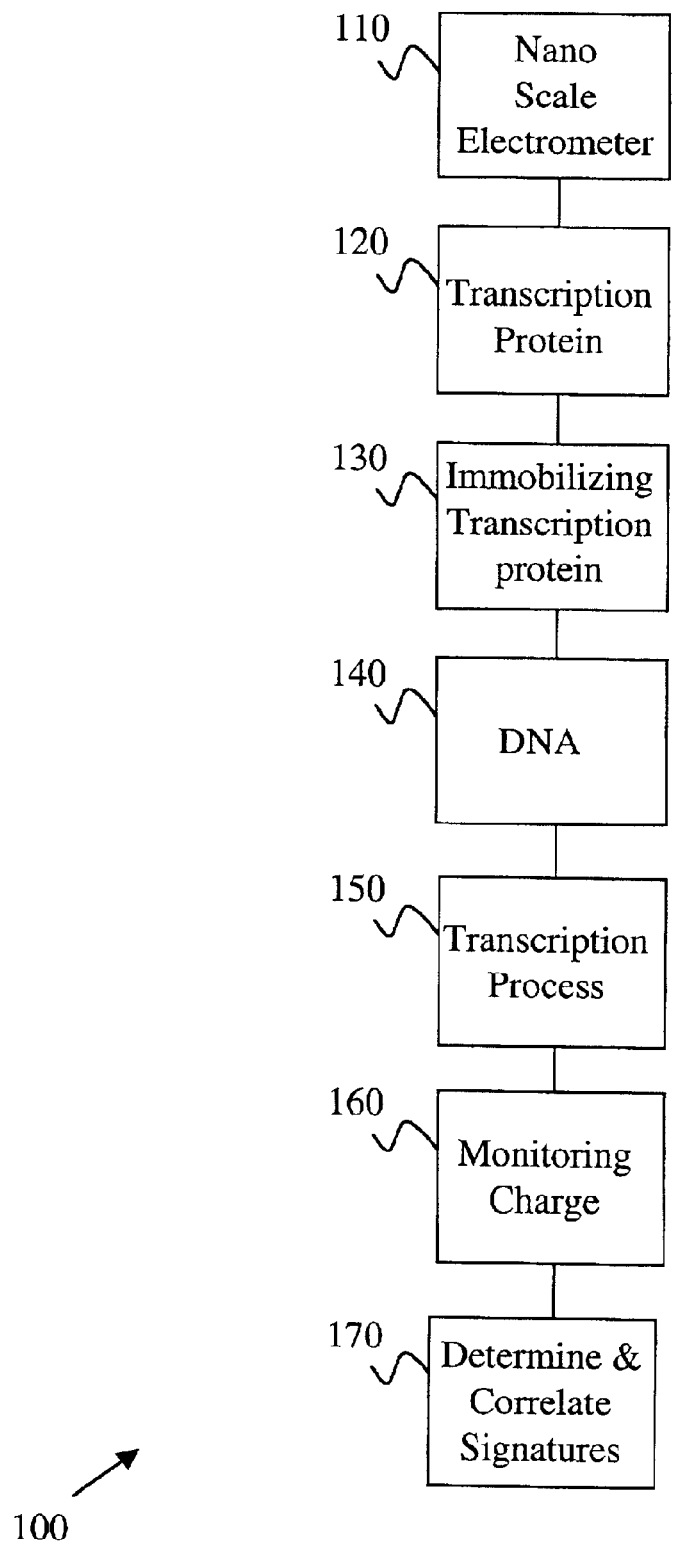
FIG. 1 shows DNA sequencing according to the present invention.

The present invention provides an apparatus and method 100 as shown in FIG. 1 for nucleotide or DNA sequencing by monitoring the molecular charge configuration as a DNA sample moves through a transcription protein 120. Transcription protein 120 can be any type of protein or polymerase capable of transcribing DNA. In particular, transcription protein 120 is a RNA polymerase. To sequence a known or an unknown strand of template DNA 140, transcription protein 120 is first immobilized 130 on a nanometer scale electrometer 110. The present invention teaches two embodiments of nanometer scale electrometers 110 that are used as sensitive devices for measuring electronic charge that is released during the transcription process. These embodiments are described below. A sample of DNA 140 is delivered to the immobilized transcription protein 130. The sample of DNA 140 could either be a known or unknown piece of DNA or a part of DNA sequence. During this process of immobilization 130, the electronic charge configuration of the RNA, together with the shape of the transcription protein, will determine the charge in the vicinity of the nanometer scale electrometer 110, and this will correspond to the nucleotide that is being replicated 150. Monitoring 160 the charge of the nanometer scale electrometer 110 as a function of time directly measures the dynamic electric field from these activities. Each nucleotide has a distinct signature, and by correlating these signatures 170 to the time domain output of nanometer scale electrometer 110, DNA 140 is sequenced.

Sequencing DNA with a Transcription Protein and a Single Electron Transistor

Figure 2:
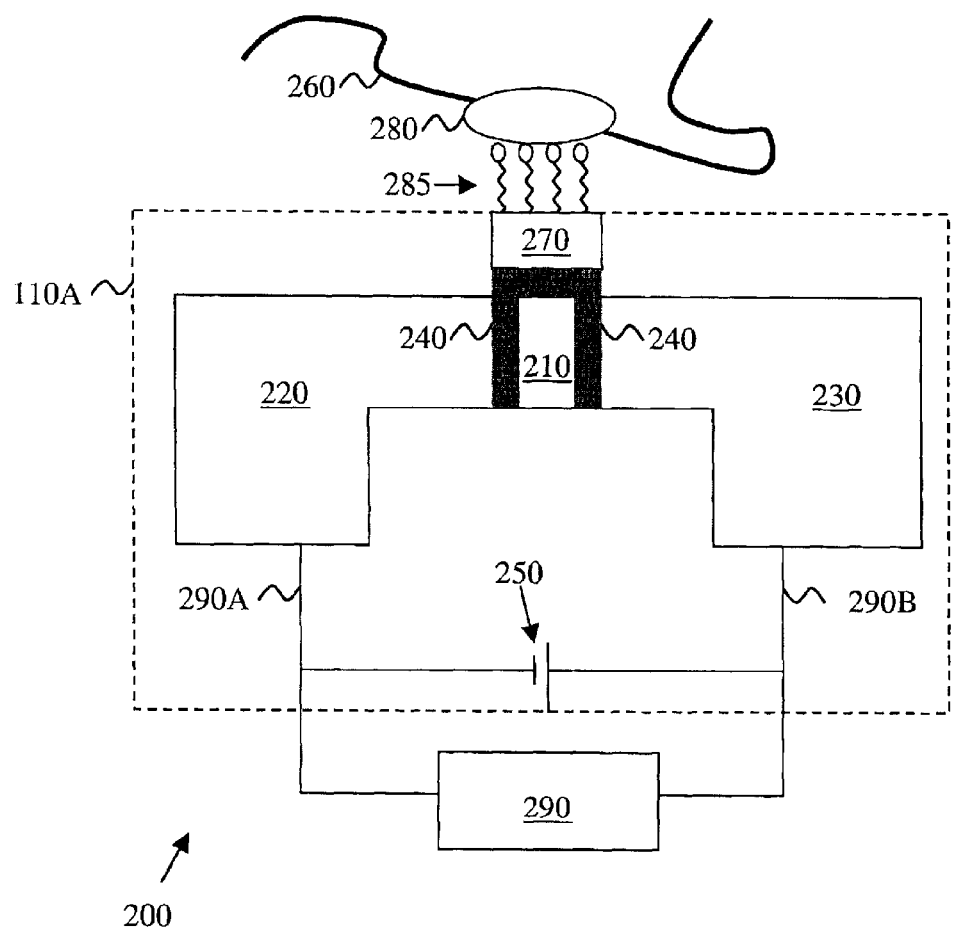
FIG. 2 shows an exemplary embodiment of DNA sequencing with a single electron transistor according to the present invention.

FIG. 2 shows an exemplary embodiment of DNA sequencing apparatus 200. FIG. 2 further shows an exemplary embodiment of nanometer scale electrometer 110 that is used as one of the most sensitive devices and methods for measuring electronic charge. The device in this particular embodiment is called a single electron transistor 110A. A reference to single electron transistor is, for instance, K. K. Likharev (1999), in a paper entitled "Single-electron devices and their applications," published in Proc. of the IEEE Vol. 87(4), page 606. The charge sensitivity of the single electron transistor is far superior to other prior art devices. It is four orders of magnitude more sensitive than electrometers based on the conventional field-effect transistor. For example, a single electron transistor has the capability of modulating a current flow of about 10⁹ electrons per second by the presence of half an electron charge on the gate. However, the single electron transistor and field-effect transistor are similar in that they both control the current flowing between the source and drain by the electric field produced by an applied gate voltage. A single electron transistor contains a metal island 210 that is isolated from source 220 and drain 230 electrodes by thin tunnel junctions 240. There are two effects that control the operation of a single electron transistor. First, the tunnel junctions 240 break the continuity of the classical electrons flow into discrete electron units. Second, the Coulomb energy of metal island 210 regulates the number of electrons that can tunnel in and out of metal island 210. Altering voltage 250 modifies the Coulomb energy, which controls the source-drain current. The single electron transistor will operate at room temperature if the length scale of tunnel junctions 240 is near 10 nm. The tunnel junctions of the single electron transistor of the present invention preferably ranges from 0.1 to 10 nm. The metal island of the single electron transistor of the present invention preferably ranges from 2 to 20 nm.

Yoo et al. (1997) in a paper entitled *"Scanning single electron transistor microscopy: imaging individual charges"*, published in Science 276, page 579 demonstrated that a single electron transistor fabricated on the apex of a tapered fiber could be scanned across a surface and image individual electron charges. Schoelkopf et al. (1998) in a paper entitled *"The radio-frequency single electron transistor: a fast and ultrasensitive electrometer"*, published in Science 280, page 1238 presented a radio frequency single electron transistor that achieves a charge sensitivity of $10^{-5}$ electrons per root hertz. Schoelkopf et al. (1998) predict that an optimized version of the radio frequency single electron transistor will be an order of magnitude more sensitive. A 5

Transcription protein 280 is first immobilized on gate 270 of single electron transistor 110A. In a preferred embodiment, gate 270 is either constructed or coated with gold. The process of immobilizing a polymerase to a gold surface is well know to a person of ordinary skill in the art. For instance, Schafer et at. (1991, same reference as above) and Yin et al. (1995, same reference as above) have shown that RNA polymerase can be attached to a gold surface using a self assembling monolayer of ω-functionalized alkanethiols 285. To sequence, transcription protein 280 is immobilized on gate 270 and an unknown strand of DNA 260 is delivered to the transcription protein 280. During this process, the electronic charge configuration of the RNA and DNA together with the shape of the transcription protein will determine the electronic charge in the vicinity of single electron transistor 110A. The electronic charge configuration corresponds to the nucleotide that is being replicated. Monitoring, with monitor 290 and leads 290A, 290B, the electronic charge configuration, or in other words, the source-drain conductance of single electron transistor 110A as a function of time directly measures the dynamic electric field from the activities. DNA transcription occurs at a rate of 10–100 nucleotides per second. Typically a single electron transistor has a charge sensitivity on the order of a hundredth of an electron with a 100 µs response time. Monitor 290 could be any type of monitoring device capable of detecting and monitoring the changes in nucleotides with the appropriate sensitivity. Monitor 290 is either an analog or an digital device. Monitoring device 290 could also include computing means in terms of software programs that run on a computer device to monitor, process and calculate any type of parameters from the obtained source-drain conductance. Each nucleotide has a distinct signature, and by correlating these signatures to the time domain output of the single electron transistor, the DNA is sequenced.

Sequencing DNA with a transcription protein and a nanoparticle

Figure 3:
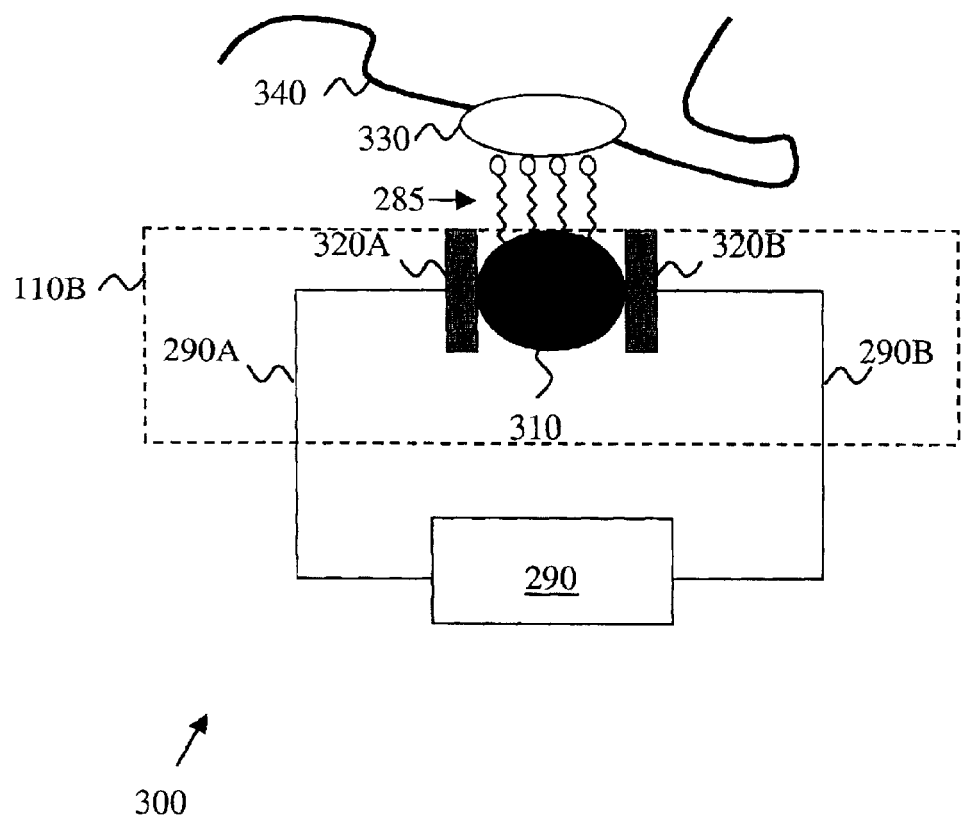
FIG. 3 shows an exemplary embodiment of DNA sequencing with a nanoparticle device according to the present invention.

FIG. 3 shows exemplary embodiment of DNA sequencing apparatus 300 according to the present invention. FIG. 3 shows another exemplary embodiment of a nanometer scale electrometer 110 that could also be used in the present invention to measure electronic charge. The device in this particular embodiment is a nanoparticle device 110B. The difference between nanoparticle device 110B and single electron transistor 110A is that in case of nanoparticle device 110B, the charge generated by the transcription process passes through nanoparticle device 110B and is detected by monitor 290. In case of single electron transistor 110A a voltage needs to be applied to generate Coulomb energy which controls the source-drain current. Single electron transistor 110A is then able to sense the charge generated by the transcription process. Nanoparticle device 110B includes a nanoparticle 310 that is positioned in between two electrodes 320A and 320B. The immobilization of transcription protein 330 to nanoparticle 310 is done in a similar way as mentioned above in relation to FIG. 2. Nanoparticle 310 is preferably a gold nanoparticle and is less than 2 nm in diameter to work at room temperature. In order for nanoparticle 310 to directly observe the electronic charges, a sensitivity on the order of a hundredth of an electron with a 100 µs response time is preferred.

Integrated Circuit Chips

Figure 4:
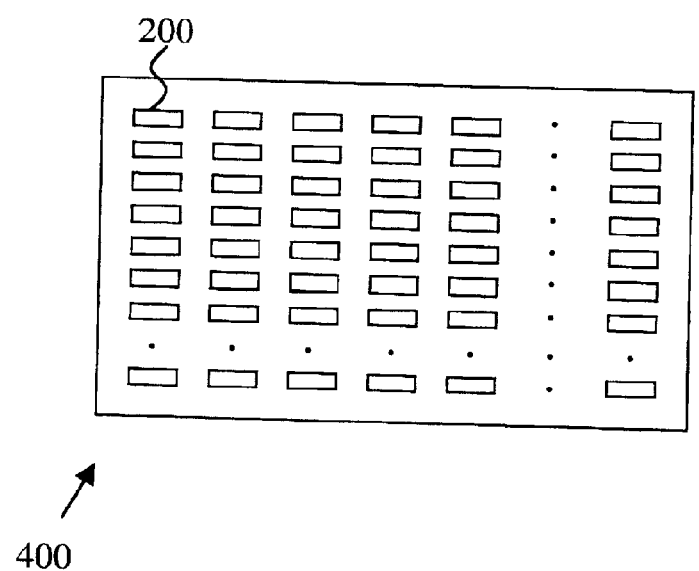
FIG. 4 shows an exemplary embodiment of an integrated circuit chip for DNA sequencing with a plurality of single electron transistors according to the present invention.
Figure 5:
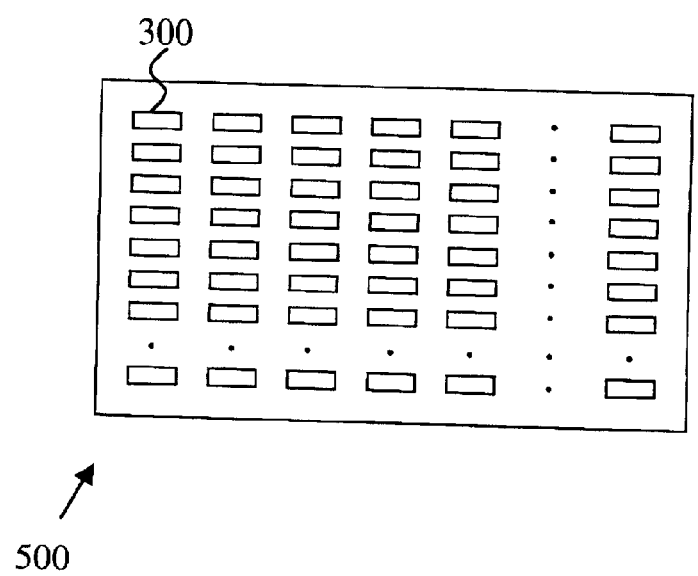
FIG. 5 shows an exemplary embodiment of an integrated circuit chip for DNA sequencing with a plurality of nanoparticle devices according to the present invention.

The DNA sequencing devices shown in FIGS. 2 and 3 could be constructed on an integrated circuit chip as shown by schematic circuit chips 400 and 500 shown in FIG. 4 and FIG. 5 respectively. Integrated circuit chips commonly span a square centimeter and a plurality of DNA sequencing devices of the present invention could be constructed on the chip. A single DNA sequencing device as shown in FIG. 2 typically occupies a surface of 10 µm². With integrated, circuit chips commonly spanning a square centimeter, it is feasible that a million DNA sequencing devices as shown in FIG. 2 could be constructed in parallel. If a million DNA sequencing devices in parallel sequenced at a rate of 100 nucleotides per second, the entire human genome of 3 billion base pairs could be sequenced in less than a minute.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, various types of nanometer scale electrometers could be employed to measure the electronic charges generated by the transcription process. Various different types of monitoring devices and means as well as different computing devices and methods could be used. All such variations are considered to be within the scope and spirit of the present invention as defined by the following claims and their legal equivalents.

What is claimed is:

1. An apparatus for sequencing DNA, comprising:
   (a) a nanoparticle device comprising:
      (i) two electrodes; and
      (ii) a nanoparticle positioned in between said two electrodes; and
   (b) a protein that is capable of transcribing said DNA, wherein said protein is immobilized on said nanoparticle device to receive and transcribe said DNA.

2. The apparatus as set forth in claim 1, wherein said protein is immobilized on said nanoparticle to receive said DNA.

3. The apparatus as set forth in claim 1, wherein said nanoparticle is a gold nanoparticle.

4. The apparatus as set forth in claim 1, wherein said nanoparticle is less than 2 nm in diameter.

5. The apparatus as set forth in claim 1, wherein said nanoparticle device has a sensitivity on the order of a hundredth of an electron with a 100 µs response time.

6. The apparatus as set forth in claim 1, wherein said nanoparticle is a room temperature nanoparticle.

7. The apparatus as set forth in claim 1, wherein said protein is a RNA polymerase.

8. The apparatus as set forth in claim 1, further comprising monitoring means attached to said nanoparticle device to monitor an electronic charge configuration as said DNA moves through said protein.

9. The apparatus as set forth in claim 8, further comprising computing means to compute a correlation between said electronic charge configuration and a nucleotide signature of said DNA.

10. An integrated circuit chip for sequencing one or more DNA samples, comprising:
   (a) a plurality of interconnected nanoparticle devices, each comprising:
      (i) two electrodes; and
      (ii) a nanoparticle positioned in between said two electrodes; and
   (b) a plurality of proteins that are capable of transcribing said one or more DNA samples, wherein said proteins are immobilized on said plurality of interconnected nanoparticle devices to receive and transcribe said one or more DNA samples.

11. The integrated circuit chip as set forth in claim 10, wherein for each of said nanoparticles one of said proteins is immobilized.

12. The integrated circuit chip as set forth in claim 10, wherein said nanoparticle is a gold nanoparticle.

13. The integrated circuit chip as set forth in claim 10, wherein said nanoparticle is less than 2 nm in diameter.

14. The integrated circuit chip as set forth in claim 10, wherein said nanoparticle device has a sensitivity on the order of a hundredth of an electron with a 100 µs response time.

15. The integrated circuit chip as set forth in claim 10, wherein said nanoparticle is a room temperature nanoparticle.

16. The integrated circuit chip as set forth in claim 10, wherein said proteins are RNA polymerases.

17. The integrated circuit chip as set forth in claim 10, further comprising monitoring means attached to said nanoparticle devices to monitor electronic charge configurations as said one or more DNA samples move through said proteins.

18. The integrated circuit chip as set forth in claim 17, further comprising computing means to compute one or more correlations between said electronic charge configurations and nucleotide signatures of said one or more DNA samples.

* * * * *